US009213009B2

(12) United States Patent  
Bishop et al.

(10) Patent No.: US 9,213,009 B2  
(45) Date of Patent: Dec. 15, 2015

(54) SYSTEM AND METHOD OF OPTIMIZING A COMPOSITE SYSTEM

(75) Inventors: Stephen K. Bishop, Dallas, TX (US); Jacob J. Hart, Dallas, TX (US)

(73) Assignee: Textron Innovations Inc., Providence, RI (US)

(*) Notice: Subject to any disclaimer, the term of this patent is extended or adjusted under 35 U.S.C. 154(b) by 420 days.

(21) Appl. No.: 13/326,923

(22) Filed: Dec. 15, 2011

(65) Prior Publication Data

US 2013/0154162 A1    Jun. 20, 2013

(51) Int. Cl.
*G01B 15/00* (2006.01)
*G01N 27/02* (2006.01)
*G01N 33/44* (2006.01)

(52) U.S. Cl.
CPC ............ *G01N 27/021* (2013.01); *G01N 33/442* (2013.01)

(58) Field of Classification Search
CPC .......................... G01N 33/442; B29C 35/0288
USPC .......... 264/406, 408, 272.11, 272.13, 272.17, 264/449
See application file for complete search history.

(56) References Cited

U.S. PATENT DOCUMENTS

| | | | | |
|---|---|---|---|---|
| 3,791,792 A | * | 2/1974 | Lindsay | 526/60 |
| 4,399,100 A | * | 8/1983 | Zsolnay et al. | 422/62 |
| 4,423,371 A | | 12/1983 | Senturia et al. | |
| 5,210,499 A | * | 5/1993 | Walsh | 324/649 |

FOREIGN PATENT DOCUMENTS

WO    2005086965    9/2005

OTHER PUBLICATIONS

Canadian Examination Report in related Canadian patent application No. 2,798,673, mailed Jul. 25, 2013, 2 pages.
Examination Report in related European patent application No. 12150686.9, mailed Oct. 4, 2013, 4 pages.
Examination Report in related European patent application No. 12150686.9, 4 pages, mailed Mar. 19, 2014.
Office Action dated May 28, 2014 from counterpart CA App. No. 2798673.
Summons to Oral Proceedings dated Feb. 24, 2015 from counterpart EP App. No. 12150686.9.

* cited by examiner

*Primary Examiner* — Stella Yi
(74) *Attorney, Agent, or Firm* — James E. Walton

(57) ABSTRACT

The present application relates to a method and system for optimizing a composite system by electrically monitoring the reactive and physiological behavior of the resin binder in a composite system, so as to develop the desired properties of the resin during the cure process. A method of manufacturing a composite part can include assembling a composite preform with a resinous material and an open circuit. Further, the method can include subjecting the composite preform to a curing cycle so that a resin in the resinous material melts and closes the open circuit. Further, the method can include electrically monitoring a current through the resin during the curing cycle. Further, the method can include selectively controlling a manufacturing variable in response to the step of electrically monitoring the current through the resin.

19 Claims, 8 Drawing Sheets

SYSTEM AND METHOD OF OPTIMIZING A COMPOSITE SYSTEM

BACKGROUND

1. Technical Field

The present application relates in general to composite systems. More specifically, the present application relates to a method and system for optimizing a composite system by electrically monitoring the reactive and physiological behavior of the resin binder in a composite system, so as to develop the desired properties of the resin during the cure process. The system and method of the present application is well suited for manufacturing composite parts for use in aircraft; however, the system and method of the present application can be used to manufacture composite parts for use in a wide variety of industries.

2. Description of Related Art

The structural integrity of composite structures is partly dependent upon a consistency of the matrix of load bearing fibers in the risen binder. For example, a void, marcel, or other defect in the cured composite structure is highly undesirable as the defect can cause the composite structure to fail. Further, the potential of defects typically result in extensive examination of the cured composite structure to verify that a defect does not exist. Although, there have been significant developments in composite systems and manufacturing techniques, defects in composite structure routinely occur. Furthermore, there is a need for a system and method for optimizing a composite system to reduce and/or eliminate defects in composite structures, as well as to control the properties in the cured composite structures.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

DESCRIPTION OF THE PREFERRED EMBODIMENT

Illustrative embodiments of the system and method of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1:
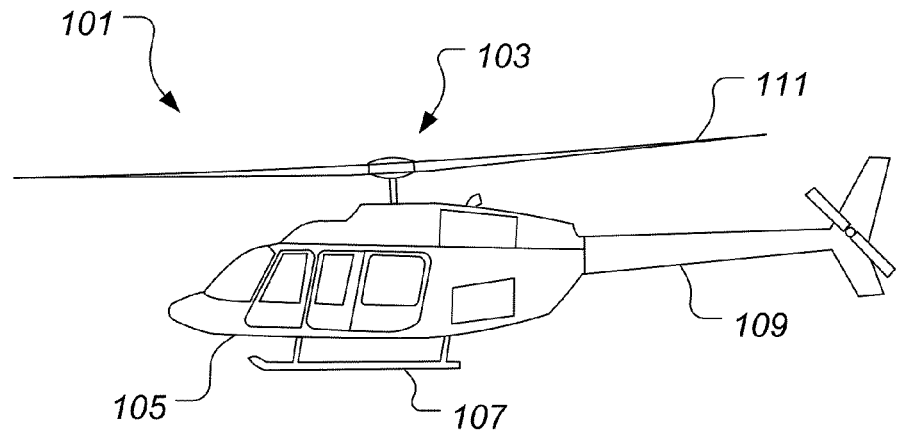
FIG. 1 is a side view of a rotorcraft, according to an embodiment of the present application.

Referring to FIG. 1 in the drawings, a rotorcraft 101 is illustrated. Rotorcraft 101 has a rotor system 103 with a plurality of rotor blades 111. The pitch of each rotor blade 111 can be selectively controlled in order to selectively control direction, thrust, and lift of rotorcraft 101. Rotorcraft 101 further includes a fuselage 105, landing gear 107, and a tail member 109.

Figure 2:
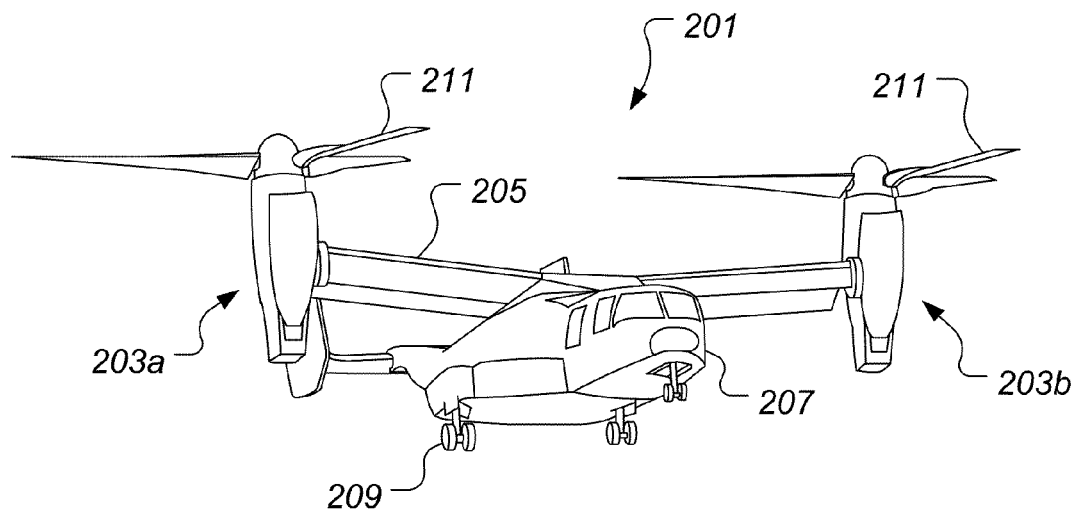
FIG. 2 is a perspective view of a tilt rotor aircraft, according to an embodiment of the present application.

Referring to FIG. 2 in the drawings, a tiltrotor aircraft 201 is illustrated. Tiltrotor aircraft 201 includes a fuselage 207, a landing gear 209, a wing 209, and rotatable nacelles 203a and 203b. Each nacelle 203a and 203b includes a plurality of rotor blades 211. The position of nacelles 203a and 203b, as well as the pitch of rotor blades 211, can be selectively controlled in order to selectively control direction, thrust, and lift of tiltrotor aircraft 201.

It is especially desirable for components of rotorcraft 101 and tiltrotor aircraft 201 to be manufactured with composite systems since composite components are typically very weight efficient. Illustrative composite components can include: wings, blades, spars, rotor grips, compartments, flooring, to name a few. As such, the system and method of the present application may be utilized to manufacture composite components for rotorcraft 101 and tiltrotor aircraft 201, as well as other aircraft.

The system and method of the present application can be utilized to tailor fatigue properties of a composite component by actively monitoring and controlling certain variables during the curing procedure, as discussed further herein. As such, any composite component for which it is desirable to have tailored flexibility and/or ductility characteristics, which can affect fatigue properties, can benefit by use of the systems and methods disclosed herein. Further, the system and method of the present application can be utilized to manufacture composite parts with precision and repeatability by real-time monitoring and performing feed-forward control of variables, such as pressure, temperature, and time, during the curing of the resin system in the composite part. Even further, the system and method of the present application make it achievable to use a resin system having considerable variation in composition, but still produce composite parts having consistency and quality. These and other advantages of the system and method of the present application are discussed further herein.

It should be appreciated that the system and method of the present application may be utilized to manufacture composite components on other types of aircraft, as well as non-aircraft applications. For example, the system and method of the present application may be utilized to manufacture composite components on a wind turbine, space vehicle, ground vehicle, surface marine vehicle, amphibious marine vehicle, and submersible marine vehicle, to name a few examples.

Composite systems can be provided to the end user in a variety formats. One illustrative composite system is a "pre-preg" composite system which includes one or more layers of fibers pre-impregnated with an uncured resin system. In another composite system, the resin and fibers are kept segregated until the user joins the resin and fibers during manufacturing. For example, in a resin transfer moulding process the fibers are selectively oriented in a mould prior to a resin being introduced into the fiber matrix. A vacuum can then be used to draw the resin into the fiber matrix. It should be appreciated that a wide variety of composite systems and methods of manufacturing can be used in conjunction with the systems and methods disclosed herein.

Figure 3:
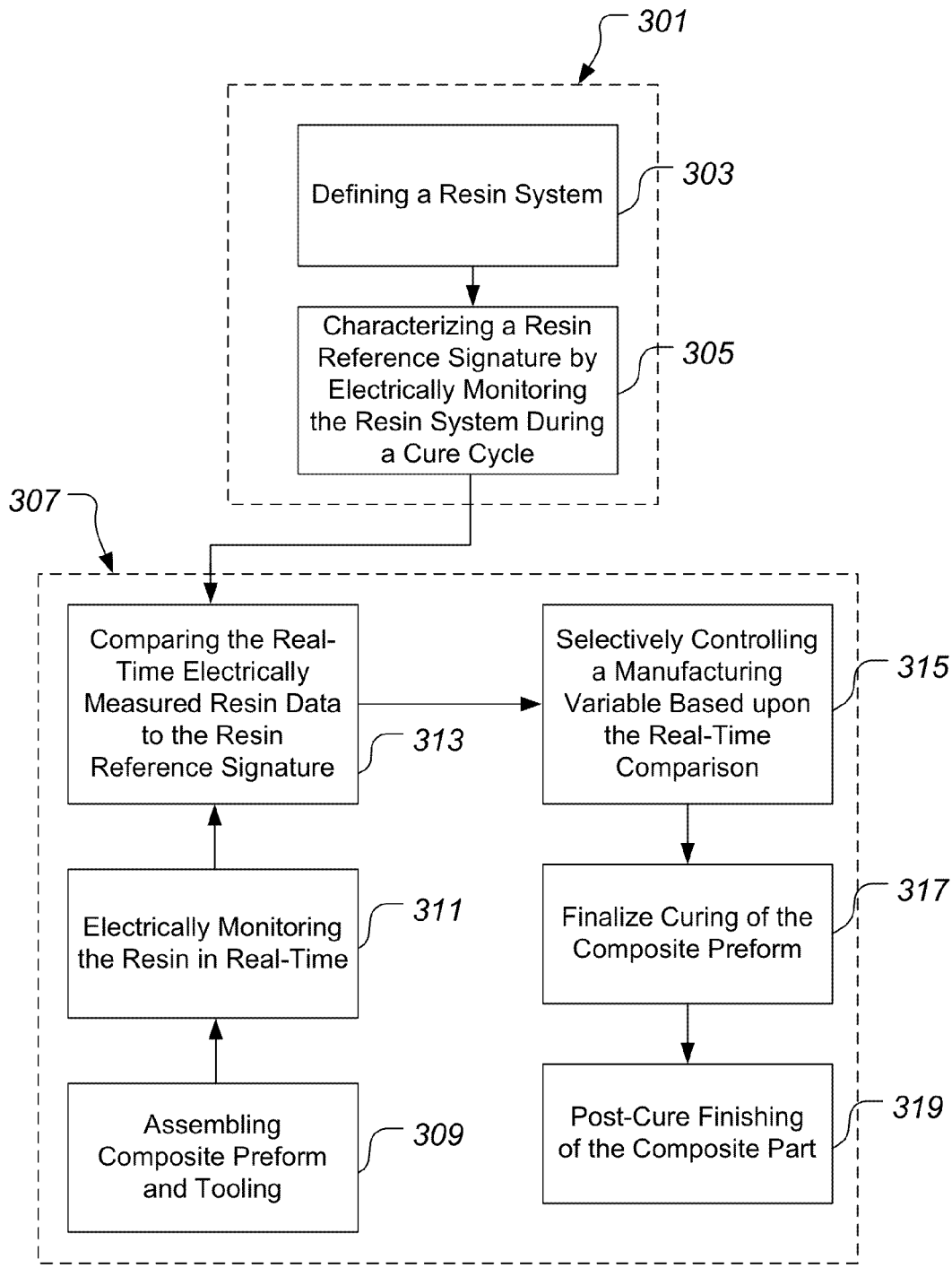
FIG. 3 is a schematic view of a method, according to an embodiment of the present application.

Referring to FIG. 3, a method 301 of determining a resin reference signature and a method 307 of manufacturing a composite part are each illustrated. Method 301 involves determining a resin reference signature so as to learn the relationship between electrical conductivity and viscosity for a given resin system. Method 307 involves electrically monitoring the reactive and physiological behavior of the resin binder in a composite system, so as to develop the desired properties of the resin during the cure process. The resin reference signature developed in method 301 is preferably utilized in method 307; however, methods 301 and 307 can be each performed and utilized independently of each other.

Method 301 first includes a step 303 of defining a resin system. The resin system can be of a variety resin types. For example, the resin system can be impregnated in a fiber layer in a "pre-preg" system. In another embodiment, the resin system is an adhesive film. In another embodiment, the resin system is applied in a liquid state. It should be appreciated that there are a variety of resin systems known in the art. Further, step 303 includes simply choosing a resin system for which it is desired to characterize.

Method 301 further includes a step 305 of characterizing a resin reference signature by electrically monitoring the resin system, as defined in step 303, during a curing cycle. Referring now also to FIGS. 4-7, step 305 is described and illustrated in further detail.

Figure 4:
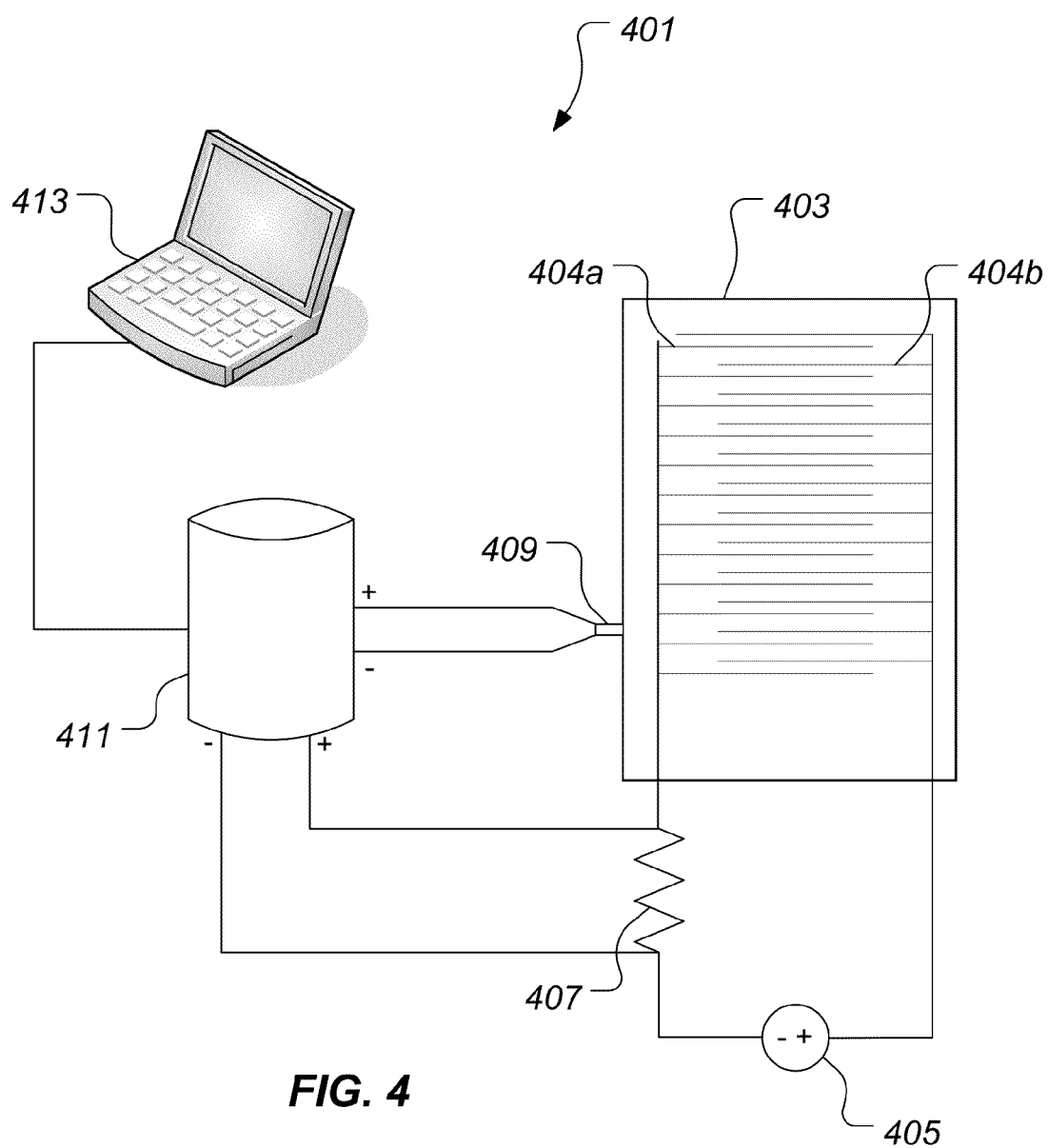
FIG. 4 is a schematic view of a system, according to an embodiment of the present application.

Referring to FIG. 4, a resin monitoring setup 401 is illustrated. It should be appreciated that setup 401 can be used not only in method 301, but also method 307, as discussed further herein. Setup 401 includes an interdigitated circuit 403 that is configured to be open and bridged by the resin system during the cure cycle. In an illustrative embodiment, circuit 403 includes a plurality of conductor tracks 404a separated from a plurality of conductor tracks 404b by 0.010 inch spaces. Conductor tracks 404a are connected to a first buss line, while conductor tracks 404b are connected to a second buss line. In the illustrated embodiment, first conductor track 404a and second conductor track 404b are each 0.010 inch wide and 0.0007 inch thick. In the illustrated embodiment, circuit 403 is approximately 6.0×6.0 inches; however, it should be fully appreciated circuits of other sizes and dimensions may be used. A voltage is applied to circuit 403 with a power source 405. In the preferred embodiment, the power source applies 10 volts of direct current (DC); however, it should be appreciated that other voltages may be used. Circuit 403 is configured such that the resin system closes the circuit so that the temperature based behavior, such as melting, decreasing viscosity, catalyst activation, and polymerization growth in molecular weight, can be monitored and understood by an observer. The method by which this is possible is the principle that polar groups characteristic of organic epoxy, and other relative systems, will carry an electrical current in proportion to the presence of these groups and the temperature-related mobility. In other words, the current in circuit 403 increases as viscosity of the resin system decreases. Further, the entire cure process can be watched by monitoring the current (as measured by voltage) as the resin system melts with an increase in temperature, as well as the beginning and ending of the polymerization, or cure, of the resin system.

Still referring to FIG. 4, resin monitoring setup 401 further includes a resistor 407 to allow the current to return to power source 405. In the preferred embodiment, resistor 407 is a 500 ohm resistor, but other resistors having other resistances can be used. Resin monitoring setup 401 further includes a thermocouple 409 configured to continuously monitor a temperature of the resin system throughout the cure cycle. A data acquisition unit 411 is coupled to circuit 403 and thermocouple 409. Data acquisition unit 411 is configured to record current flow through circuit 403 by recording the voltage across resistor 407, as well as temperatures via thermocouple 409. A computer 413 is in data communication with data acquisition unit 411. Computer 413 is configured with software that plots the data obtained by data acquisition unit 411. Computer 413 preferably includes a display that visibly communicates, in real-time, the current flow through circuit 403 by recording the voltage across resistor 407, as well as temperatures via thermocouple 409.

Figure 5:
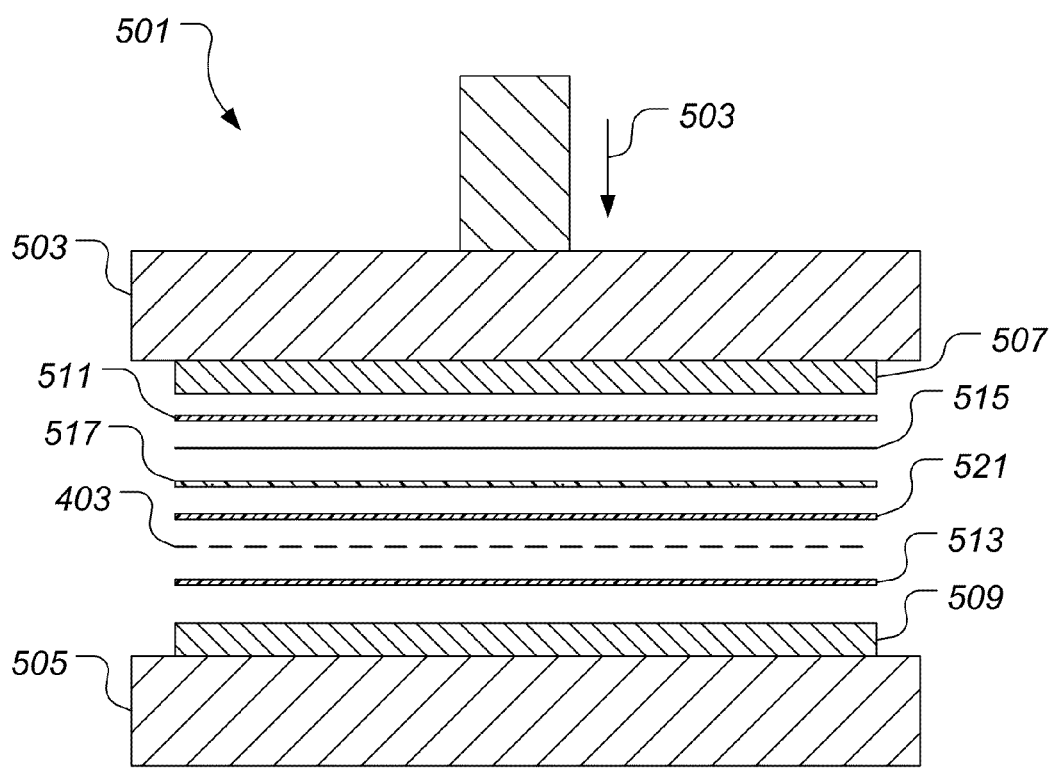
FIG. 5 is an exploded sectional view of an exemplary stack setup, according to an embodiment of the present application.

Referring now also to FIG. 5, an embodiment of a stack setup 501 is illustrated. Stack setup 501 is a test setup configured to imitate the parameters to which the resin system can experience in an actual composite part manufacturing procedure. In the illustrated embodiment, setup 501 is configured to imitate a procedure for manufacturing a composite part in a closed mould environment which applies mechanical pressure to the upper and lower surfaces of the composite part. It should be appreciated that setup 501 is illustrated for exemplary purposes and that is well contemplated that other configurations of stack setup 501 can be used.

Still referring to FIG. 5, the illustrated embodiment of stack setup 501 includes a heated upper platen 503 and a heated lower platen 505. An upper rigid plate 507 and a lower rigid plate 509 can be located adjacent to heated upper platen 503 and heated lower platen 505, respectively. Preferably, upper and lower rigid plates 507 and 509 include a thermally conductive material, such as aluminum. An upper caul 511 and a lower caul 513 can be located adjacent upper and lower rigid plates 507 and 509, respectively. In the illustrated embodiment, upper caul 511 and lower caul 513 are of a silicone material and approximately 0.065 inch thick. A release film 515 can be located between an upper caul 511 and a resin member 517. Similarly, a release film 519 can be located between interdigitated circuit 403 and lower caul 513.

A scrim fabric 521 can be located between interdigitated circuit 403 and resin member 517.

Scrim fabric 521 is configured to allow the resin in resin member 517 to bleed through scrim fabric 521 so as to become in contact with circuit 403, while preventing particulate matter from coming into contact with circuit 403, which could cause a short. An illustrative scrim fabric 521 is a Cerex 23030 scrim fabric marketed by Cerex Advanced Fabrics, Inc. Resin member 517 can be any of a variety of resin systems. For example, resin member can be a ply of a pre-preg material, such as a HEXCELL 8552 resin system having a resin impregnated fiberglass ply. In another illustrative embodiment, resin member 517 can be an adhesive film layer.

Stack setup 501 is configured so that temperature and pressure can be selectively applied to resin member 517. In the illustrative setup 501, upper platen 503 and lower platen 505 are pressed together in direction 523 to apply a clamping force on all the components therebetween.

Step 305 of method 301 includes using resin monitoring setup 401 in conjunction with stack setup 501 to derive the resin reference signature of the resin by electronically monitoring the resin system during a cure cycle. The cure cycle can include selectively applying heat and pressure over time. During step 305, current flow current flow through circuit 403 (by recording the voltage across resistor 407) is monitored throughout the cure cycle in order to derive the resin reference signature for the resin member 517.

Figure 6:
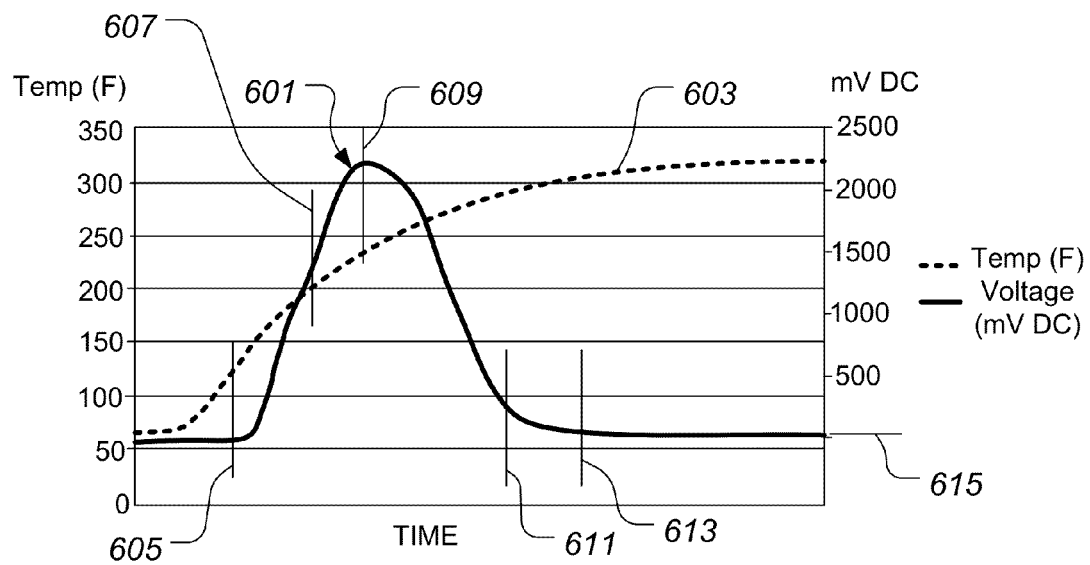
FIG. 6 is a graphical view of an exemplary resin reference signature, according to an embodiment of the present application.

Referring now also to FIG. 6, an illustrative resin reference signature 601 and a temperature profile 603 for an illustrative cure cycle of stack setup 501 are shown. Resin reference signature 601 can represent a variety of data pertaining to the physiological behavior of the resin member 517 throughout the cure cycle. Of particular importance is an appreciation of viscosity, as measured by voltage, as a function time and temperature. Furthermore, by using differential calculus, distinct identification of key changes in the physiological behavior of resin member 517 can be made. For example, a derivative of the resin reference signature 601 can reveal a melting point 605, a catalyst point 607, a peak minimum viscosity point 609, a cure finalization point 611, and a plateau point 613. A cure zone of resin member 517 can be classified as the time period between peak minimum viscosity point 609 and cure finalization point 611. A variable viscosity window can be categorized as the viscous time window between melting point 605 and cure finalization point 611. The time region after cure finalization point 611 can be classified as a plateau area where the viscosity in the resin remains relatively constant, thereby signifying that the cure of the resin member 517 has finalized.

A ductility measurement 615 is the viscosity, as measured by voltage, in the plateau area where the voltage remains relatively constant. Knowledge of ductility, as realized by ductility measurement 615, is valuable because it allows the user to customize ductility of the cured composite part by customizing the temperature heat rate during curing cycle. For example, it is typically desirable for a circuit board product to be brittle, thus have a low ductility measurement 615. In contrast, it is typically desirable for a rotor blade spar to have a rubbery and flexible quality, thus have a high ductility measurement 615. Selectively manipulating the ductility of resin member 517 is discussed further below in regard to FIG. 7.

Figure 7:
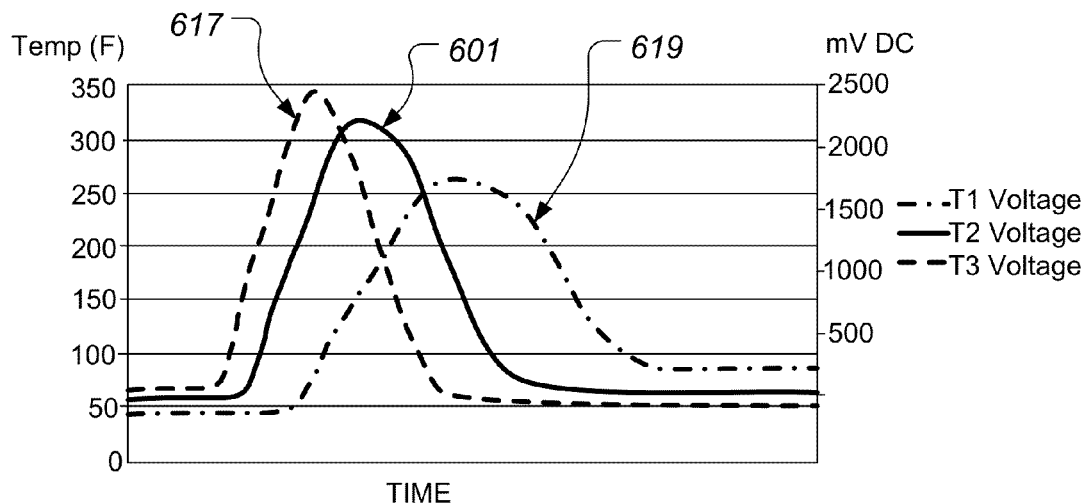
FIG. 7 is a graphical view of exemplary resin reference signatures, according to an embodiment of the present application.

Referring now also to FIG. 7, a first supplemental resin reference signature 617 and a second supplemental resin reference signature 619 are each illustrated along with resin reference signature 601. Resin reference signature 617 is indicative of curing resin member 519 at an increased temperature heat rate, as compared to resin reference signature 601. As shown, resin reference signature 617 has a higher peak minimum viscosity point, a shorter viscosity window, and a lower ductility measurement, as compared to resin reference signature 601. Conversely, resin reference signature 619 is indicative of curing resin member 519 at a decreased temperature heat rate, as compared to resin reference signature 601. As shown, resin reference signature 619 has a lower peak minimum viscosity point, a longer viscosity window, and a higher ductility measurement, as compared to resin reference signature 601.

It should be appreciated that knowledge of the data generated in method 301 can be valuable in a variety of applications. Variation in compositions of a particular resin can produce variations in resin reference signature, such as resin reference signature 601 in FIGS. 6 and 7. For example, method 301 can be performed as a quality control mechanism for a supplier of a resinous product, such as pre-preg material. A pre-preg supplier can take a several displaced samples and then perform method 301 for each sample. Comparing the data generated by method 301 for each sample allows the supplier to determine if the composition of the resin is uniform throughout the roll of pre-preg. Similarly, a supplier can compare resin composition of different rolls of pre-preg by performing method 301 with samples from different rolls of pre-preg. Comparing the data generated by method 301 for each sample allows the supplier to determine if the composition of the resin is uniform between different rolls of pre-preg.

Referring again to FIG. 3, method 307 of manufacturing a composite part involves electrically monitoring the reactive and physiological behavior of the resin binder in a composite system, so as to develop the desired properties of the resin binder during the cure process. Method 307 can be utilized to manufacture composite parts with precision and repeatability by real-time monitoring and performing feed-forward control of variables, such as pressure, temperature, and time, during the curing of the resin system in the composite part. Further, method 307 makes it achievable to use a resin system having considerable variation in composition, but still produce composite parts having consistency and quality.

Figure 8:
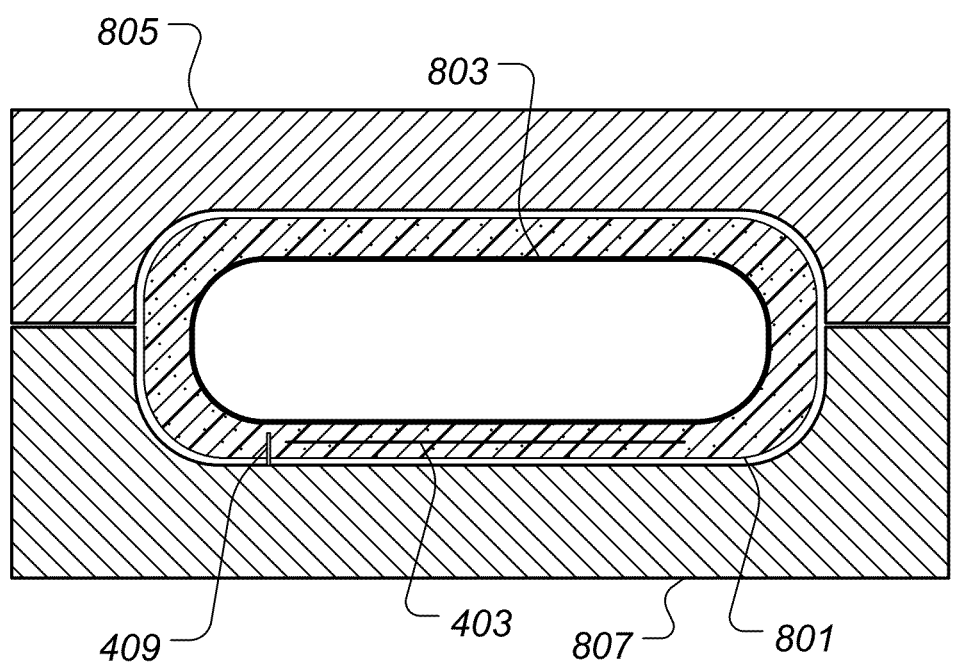
FIG. 8 is a partially schematic sectional view of an exemplary preform, according to an embodiment of the present application.

Method 307 includes a step 309 for assembling a composite preform and tooling. Referring now also to FIG. 8, for illustrative purposes a preform 801 is shown and described as a preform for a spar member of a rotor blade. However, it should be fully appreciated that method 307 can be performed for a wide variety of composite structures and manufacturing process. Preform 801 includes a plurality of layers of pre-preg uncured composite material wrapped around an expandable mandrel 803. Upper and lower mould members 807 and 807 enclose preform 801. Circuit 403 is embedded in preform 801 at an area of the spar member that can be removed during a step 319. Further, scrim fabric 521 is located adjacent circuit 403 in order to prevent conductive particulate matter from shorting out circuit 403. Further, thermocouple 409 is located in preform 801.

Figure 9:
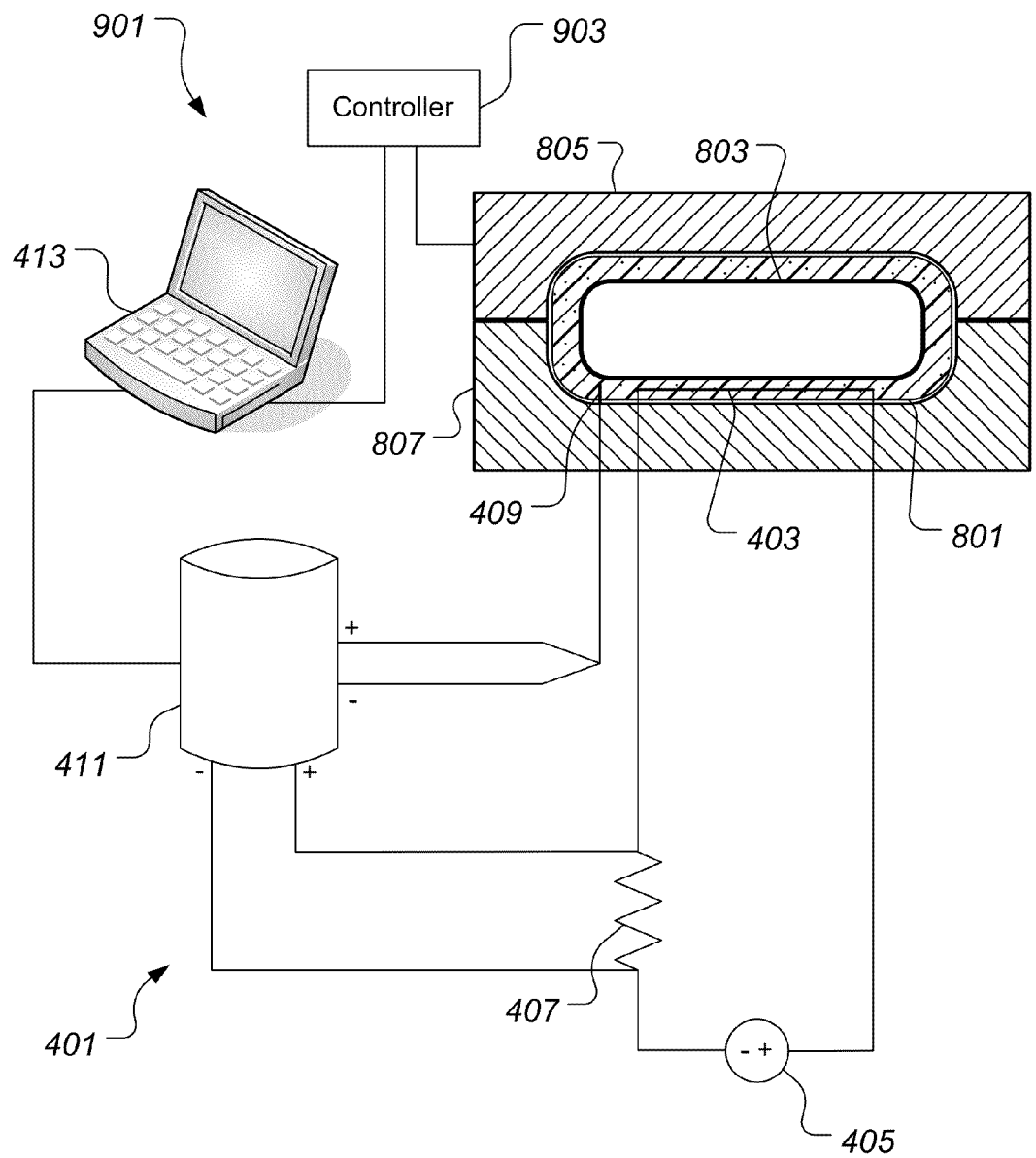
FIG. 9 is a schematic view of an exemplary monitoring/control system, according to an embodiment of the present application.

Method 307 further includes a step 311 for electrically monitoring the resin in real-time. Referring to FIG. 9, a monitoring/control system 901 is schematically illustrated. Monitoring/control system 901 can be configured and operated substantially similar to resin monitoring setup 401, except for having additional components configured for controlling variables in the composite part manufacturing process. It should be appreciated that monitoring/control system 901 is configured for real-time monitoring of throughout the cure cycle. Moreover, step 311 involves real-time monitoring of the temperature and viscosity of the resin in the composite preform throughout the cure cycle. Real-time viscosity is calculated by measuring a voltage to determine direct current (DC) flow through the resin in composite preform 801 via circuit 403, as discussed further herein. The graphs in FIGS. 6 and 7 are illustrative of data from real-time monitoring of the temperature and viscosity (via a voltage measurement) of the resin in the composite preform.

Method 307 can further include a step 313 for comparing the real-time electrically measured data to the resin reference signature. The resin reference signature can be a resin reference signature generated in method 301, for example. Illustrative resin reference signatures are graphically shown in FIGS. 6 and 7. Step 313 can be particularly important because real world composite manufacturing involves a number of variables that can affect the rate of curing of the resin in composite preform 801. For example, calibration variation of tooling can significantly affect the pressure and temperature subjected upon composite preform 801. Further, a variation in resin composition can cause the actual real-time electrically measured data to be different from the resin reference signature, even if all other variables were to be identical. Further, other variables, such ambient atmospheric conditions, can affect the rate of curing of the resin in composite preform 801, which can be exposed in a deviation in the actual real-time electrically measured data as compared to a resin reference signature. In the preferred embodiment, step 313 is performed automatically by computer 413. It should be appreciated that computer 413 can be configured with a wide range of software for performing step 313. In an alternative embodiment, step 313 is performed by a user visually comparing a graphical representation of the real-time electrically measure data to the resin reference signature.

Method 307 further includes a step 315 for selectively controlling a manufacturing variable based upon the real-time comparison from step 313. For example, system 901 includes a controller 903 configured to actively control one or more manufacturing controls, such as pressure, temperature, and time, during the curing cycle of composite preform 801. For example, the process for manufacturing preform 801 can include expanding mandrel 803 so that preform is mechanically expanded against the interior tooling surfaces of upper and lower mould members 807 and 807 so as to apply positive pressure to preform 801. It is desired that mandrel 803 is expanded over a period of time when the viscosity of resin in preform 801 has decreased to a minimum level. If mandrel 803 is expanded when the resin is preform 801 has high viscosity, then undesirable defects, such as voids and marcels, can be introduced into preform 801. Step 315 can include selectively controlling the temperature so that the viscosity window is long enough so that mandrel 803 can be fully expanded. As such, step 315 can include properly aligning viscosity and pressure, as a function of time, so as to prevent the formation of defects. Further, step 315 can include controlling to rate of expansion of mandrel 801 so as to increase or decrease the rate of expansion so that such expansion occurs during a desired viscosity window. Further, step 315 can include feed-forward control to achieve a desired viscosity of the resin in preform 801 at a future point in time.

Step 315 can further include controlling a manufacturing variable based upon the real-time comparison from step 313 so that the resin in the final cured composite part has a desired ductility. Referring again to FIGS. 6 and 7, the ductility measurement 615 is a function of the resin reference signature. For example, if the temperature subjected to preform 801 is abnormally high, due to a variation in the manufacturing equipment for example, then the ductility measurement of the final cured part can be lower than desired. As such, step 315 can include selectively controlling the temperature heat rate of the resin in preform 801 so that the final cured composite part has a desired ductility measurement 615.

Referring again also to FIG. 3, method 307 can further include a step 317 to finalize curing of the composite preform. Step 317 can include recognizing that the viscosity of the resin in preform 801 has reached a plateau, thereby signaling that the curing of the resin has completed. Recognition that the viscosity of the resin in preform 801 has reached a plateau can be performed by the software in computer 413 that is configured to analyze the rate of change of the measured voltage, which can signify that the rate of change of viscosity has reached plateau. As such, step 317 can include terminating that cure cycle based upon such a determination. Step 317 can be very valuable to large scale manufacturing operations because the composite manufacturing equipment can made available for the curing of a different composite part. In the past, a composite part may continue to be subjected to temperature and pressure over a period of time even though the cure of the resin has reached a plateau. Such a scenario is a waste of valuable time and resources.

Method 307 can further include a step 319 of post finishing of the cured composite part. In the illustrated embodiment, step 319 can include removing the portion of the cured composite part that contain circuit 403 and any other components related to system 901, such as thermocouple 409 and scrim fabric 521.

Figure 10:
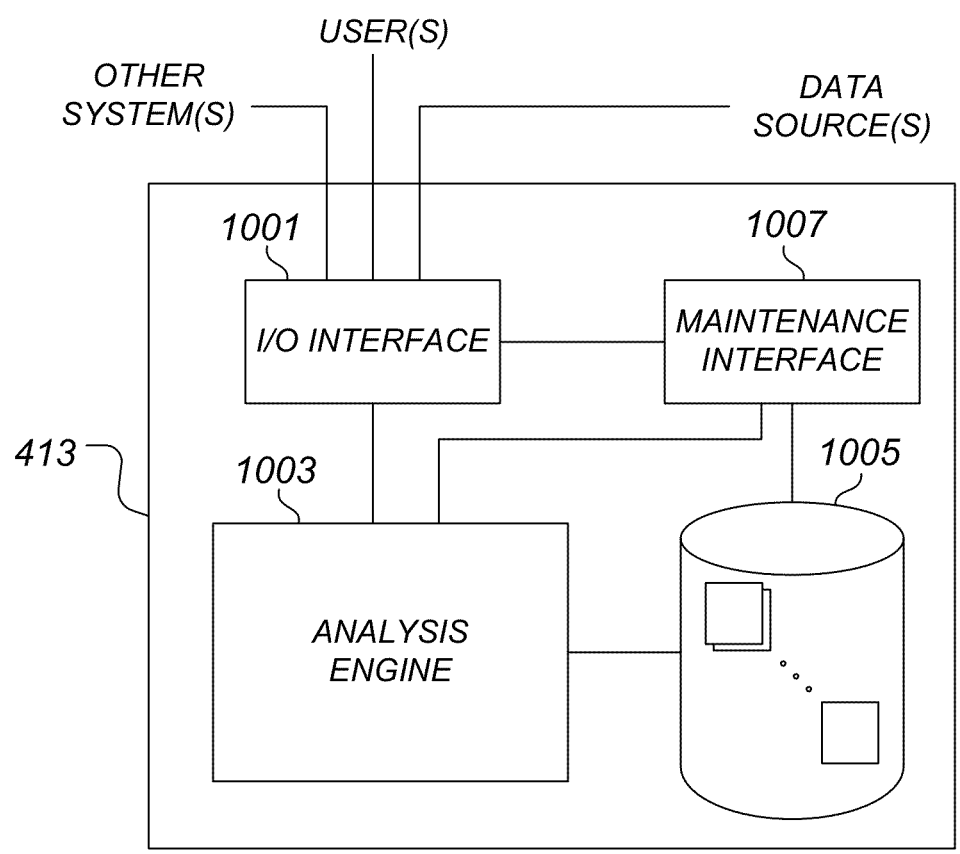
FIG. 10 is a schematic view of an exemplary computer system, according to an embodiment of the present application.

Referring to FIG. 10, an exemplary embodiment of computer 413 is illustrated. Computer 413 includes an input/output (I/O) interface 1001, an analysis engine 1003, a database 1005, and a maintenance interface 1007. Alternative embodiments can combine or distribute the input/output (I/O) interface 1001, analysis engine 1003, database 1005, and maintenance interface 1007, as desired. Embodiments of the computer 413 can include one or more computer systems that include one or more processors and memories configured for performing tasks described herein below. This can include, for example, a computer having a central processing unit (CPU) and non-volatile memory that stores non-transitory software instructions for instructing the CPU to perform at least some of the tasks described herein. This can also include, for example, two or more computers that are in communication via a computer network, where one or more of the computers include a CPU and non-volatile memory, and one or more of the computer's non-volatile memory stores software instructions for instructing any of the CPU(s) to perform any of the tasks described herein. Thus, while the exemplary embodiment is described in terms of a discrete machine, it should be appreciated that this description is non-limiting, and that the present description applies equally to numerous other arrangements involving one or more machines performing tasks distributed in any way among the one or more machines. It should also be appreciated that such machines need not be dedicated to performing tasks described herein, but instead can be multi-purpose machines, for example computer workstations, that are suitable for also performing other tasks.

The I/O interface 1001 provides a communication link between external users, systems, and data sources and components of the computer 413. The I/O interface 1001 can be configured for allowing one or more users to input information to the computer 413 via any known input device. Examples can include a keyboard, mouse, touch screen, microphone, and/or any other desired input device. The I/O interface 1001 can be configured for allowing one or more users to receive information output from the computer 413 via any known output device. Examples can include a display monitor, a printer, a speaker, and/or any other desired output device. The I/O interface 1001 can be configured for allowing other systems to communicate with the computer 413. For example, the I/O interface 1001 can allow one or more remote computer(s) to access information, input information, and/or remotely instruct the computer 413 to perform one or more of the tasks described herein. The I/O interface 1001 can be configured for allowing communication with one or more remote data sources. For example, the I/O interface 1001 can allow one or more remote data source(s) to access information, input information, and/or remotely instruct the computer 413 to perform one or more of the tasks described herein.

The database 1005 provides persistent data storage for computer 413. While the term "database" is primarily used, a memory or other suitable data storage arrangement may provide the functionality of the database 1005. In alternative embodiments, the database 1005 can be integral to or separate from the computer 413 and can operate on more than one computer. The database 1005 preferably provides non-volatile data storage for any information suitable to support the operation of the computer 413, including various types of data discussed below in connection with FIG. 3.

The maintenance interface 1007 is configured to allow users to maintain desired operation of the computer 413. In some embodiments, the maintenance interface 1007 can be configured to allow for reviewing and/or revising the data stored in the database 1005 and/or performing any suitable administrative tasks commonly associated with database management. This can include, for example, updating database management software, revising security settings, and/or performing data backup operations. In some embodiments, the maintenance interface 1007 can be configured to allow for maintenance of the analysis engine 1003 and/or the I/O interface 1001. This can include, for example, software updates and/or administrative tasks such as security management and/or adjustment of certain tolerance settings.

The analysis engine 1003 can include various combinations of one or more processors, memories, and software components. The analysis engine 1003 is configured for performing real-time monitoring and analysis for performing feed-forward control of variables, such as pressure, temperature, and time, during the curing of the resin system in the composite part.

It should be appreciated that method 307 provides the ability to recognize and actively change one or more manufacturing variables during the cure cycle so that the final composite part has desired properties. Because of the variety of composite manufacturing techniques, method 307 can likewise be used for composite manufacturing techniques other than the closed mould composite manufacturing processes disclosed herein for illustrative purposes.

The systems and methods of the present application provides significant advantages, including: (1) tailoring fatigue properties of a composite component by actively monitoring and controlling certain variables during the curing procedure; (2) manufacturing composite parts with precision and repeatability by real-time monitoring and performing feed-forward control of variables, such as pressure, temperature, and time, during the curing of the resin system in the composite part; and (3) using resin systems that have considerable variation in composition, but still producing composite parts having consistency and quality.

The particular embodiments disclosed above are illustrative only, as the application may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the application. Accordingly, the protection sought herein is as set forth in the claims below. It is apparent that a system with significant advantages has been described and illustrated. Although the system of the present application is shown in a limited number of forms, it is not limited to just these forms, but is amenable to various changes and modifications without departing from the spirit thereof.

The invention claimed is:

1. A method of characterizing a resin reference signature, the method comprising:
    locating an open circuit within a resinous member;
    applying a direct current to the open circuit;
    subjecting the resinous member and the open circuit to a curing cycle such that the resinous member contacts and bridges the open circuit as the resinous member melts, thereby providing conductive path through the open circuit;
    measuring the direct current traveling through resinous member during the curing cycle; and
    customizing a heating rate during the curing cycle so that the resinous member has a certain ductility at the end of the cure cycle;
    wherein the open circuit is interdigitated having a plurality of adjacent conductor tracks.

2. The method according to claim 1, wherein the step of measuring the direct current traveling through resinous member is achieved by measuring a voltage across a resistor.

3. The method according to claim 1, further comprising:
    locating a filter adjacent the open circuit to prevent conductive particulate matter from shorting the open circuit;
    wherein each conductor track is adjacent to one side of the filter.

4. The method according to claim 3, wherein the filter is a scrim fabric.

5. The method according to claim 1, wherein the resinous member is a pre-preg material.

6. The method according to claim 1, wherein the resinous member is an adhesive film.

7. The method according to claim 1, further comprising:
    graphically representing the resin reference signature.

8. The method according to claim 1, further comprising:
    taking a derivative of the resin reference signature to derive a change in a physiological behavior of the resinous member throughout the cure cycle.

9. The method according to claim 8, further comprising:
    identifying the change in the physiological behavior of the resinous member as at least one of:
        a melting point;
        a catalyst point;
        a peak minimum viscosity point;
        a cure finalization point; and
        a plateau point.

10. A method of manufacturing a composite part, the method comprising:
    assembling a composite preform with a resinous material and an open circuit,
        wherein the open circuit is located within the composite preform; and
        wherein the open circuit is interdigitated having a plurality of adjacent conductor tracks;
    subjecting the composite preform to a curing cycle such that the resinous member contacts and bridges the open circuit as the resin in the resinous material melts and closes the open circuit;

electrically monitoring a current through the resin during the curing cycle; and selectively controlling a manufacturing variable in response to the step of electrically monitoring the current through the resin;

terminating the curing cycle when the current through resin indicates the curing of the resin has reached a plateau.

11. The method according to claim 10, wherein the current is a direct current.

12. The method according to claim 10, wherein the resinous material is a pre-preg material.

13. The method according to claim 10, wherein the step of assembling a composite preform with a resinous material and an open circuit further includes locating a filter adjacent the circuit to prevent conductive particulate matter from shorting the open circuit;

wherein each conductor track is adjacent to one side of the filter.

14. The method according to claim 10, wherein the step of selectively controlling a manufacturing variable in response to the step of electrically monitoring the current through the resin includes:

applying mechanical pressure to composite preform when the current through the resin indicates a viscosity of the resin has reached a certain threshold.

15. The method according to claim 10, wherein the step of selectively controlling a manufacturing variable in response to the step of electrically monitoring the current through the resin includes:

decreasing a heating rate during the curing cycle when the current through the resin indicates that the resin is curing too quickly.

16. The method according to claim 10, wherein the step of selectively controlling a manufacturing variable in response to the step of electrically monitoring the current through the resin includes:

increasing a heating rate during the curing cycle when the current through the resin indicates that the resin is curing too slowly.

17. The method according to claim 10, wherein the step of selectively controlling a manufacturing variable in response to the step of electrically monitoring the current through the resin includes:

customizing a heating rate during the curing cycle so that the resin has a certain ductility at the end of the cure cycle.

18. The method according to claim 10, wherein the step of selectively controlling a manufacturing variable in response to the step of electrically monitoring the current through the resin includes:

applying vacuum pressure to composite preform when the current through the resin indicates a viscosity of the resin has reached a certain threshold.

19. The method according to claim 10, wherein the step of selectively controlling a manufacturing variable in response to the step of electrically monitoring the current through the resin includes:

changing a rate of a mechanical pressure being applied to the composite preform when the current through the resin indicates a real-time viscosity of the resin is different than predicted.

* * * * *